United States Patent [19]

Giannini

[11] Patent Number: 5,915,241
[45] Date of Patent: Jun. 22, 1999

[54] METHOD AND SYSTEM ENCODING AND PROCESSING ALTERNATIVE HEALTHCARE PROVIDER BILLING

[76] Inventor: Jo Melinna Giannini, Alternative Link 225 E. Idaho, Suite 3, Las Crucas, N.M. 88005

[21] Appl. No.: 08/928,259

[22] Filed: Sep. 12, 1997

Related U.S. Application Data

[60] Provisional application No. 60/026,048, Sep. 13, 1996.

[51] Int. Cl.$^6$ .................................................. G60F 159/00
[52] U.S. Cl. ........................ 705/2; 705/1; 705/2; 705/3; 705/4
[58] Field of Search .................................. 705/2, 1, 3, 4

[56] References Cited

U.S. PATENT DOCUMENTS

| | | | |
|---|---|---|---|
| 4,491,725 | 1/1985 | Pritchard | 705/2 |
| 4,667,292 | 5/1987 | Mohlenbrock et al. | 705/2 |
| 5,001,630 | 3/1991 | Wiltfong | 705/2 |
| 5,002,630 | 3/1991 | Kermani et al. | 705/2 |
| 5,070,452 | 12/1991 | Doyle, Jr. et al. | 705/2 |
| 5,235,507 | 8/1993 | Sackler et al. | 705/2 |
| 5,301,105 | 4/1994 | Cummings, Jr. | 705/2 |
| 5,325,293 | 6/1994 | Dorne | 705/2 |
| 5,519,607 | 5/1996 | Tawil | 705/2 |
| 5,557,514 | 9/1996 | Seare et al. | 705/2 |
| 5,644,778 | 7/1997 | Burks et al. | 705/2 |
| 5,664,109 | 9/1997 | Johnson et al. | 705/2 |
| 5,819,228 | 10/1998 | Spiro | 705/2 |
| 5,832,447 | 11/1998 | Rieker et al. | 705/2 |
| 5,835,897 | 11/1998 | Dang | 705/2 |

*Primary Examiner*—Allen R. MacDonald
*Assistant Examiner*—Romain Jeanty
*Attorney, Agent, or Firm*—Richard C. Litman

[57] ABSTRACT

A system for encoding and encompassing healthcare provider billing, more particularly, a computer assisted network for encoding, documenting and processing claims for payment of specific procedures by alternative therapy providers, grouped geographically and by specialty. The system employs a computer accessing three main databases for identifying, encoding and calculation of average costs of provider services. A resulting Alternative Billing Code (ABC) is produced which can be compared and correlated with insurance industry standard codes. The ABC has the attribute of conveying multiple levels of information through alphanumeric characters. The ABC is an assembly of a series of terms and sub-terms from databases, namely Alternative Practice Type (APT), Standard Alternative Procedure Descriptions (SAPDs), Provider Data (PD) and RVU (Relative Value Unit) databases. Each provider specialty includes its own listing of treatments which are turned into RVUs, thus establishing a sequence of treatment fees and charges. The APT code and SAPD code are stored in a PD file including average claims costs of all providers as categorized by a predetermined grouping, which with the PD create the ABC as a comprehensive, single code representing all elements of treatment incident to a patient visit. Claims for payment are submitted and translated into an appropriate code for determination of payment under the present system.

10 Claims, 2 Drawing Sheets

METHOD AND SYSTEM ENCODING AND PROCESSING ALTERNATIVE HEALTHCARE PROVIDER BILLING

CROSS-REFERENCE TO RELATED APPLICATION

This application claims the benefit of U.S. Provisional Patent Application Serial No. 60/026,048, filed Sep. 13, 1996.

BACKGROUND OF THE INVENTION

1. Field of the Invention

The present invention relates to a method and system to standardize, encode, and process healthcare provider billing, more particularly, a computer assisted system for encoding, describing and processing fee charges for specific procedures of non-conventional medicine. The process and system compiles provider and patient data by geographical location, specifically by state, for any alternative practice and produces a universal set of codes to identify fees falling within a legal or regulatory scope associated with a provider's practice.

2. Description of the Prior Art

An objective of non-conventional medicine providers is to become enrolled into managed care networks wherein fee prices and payment for each procedure can be negotiated for the mutual benefit of patients, providers and payers. However, a number of obstacles exist.

At present, non-conventional medicine is understood to include a wide range of types of medicine and professions, including, but not limited to, alternative, holistic, complementary, or integrative healing. Moreover, each profession as understood by the term non-conventional medicine further varies by state due to legislative differences in licensing and like regulatory controls.

Also, conventional payers of healthcare costs, such as insurance companies, managed care organizations, Medicare and Medicaid, etc., fail to presently understand the alternative procedures being used by alternative professionals, and therefore do not have the information to underwrite health policies. Consequently, claims made by alternative healthcare professionals are being denied by payers.

Yet, no claims payment system exists to adequately address these problems. The system and method according to the present invention has been developed to overcome each of these problems, thus providing the benefit of permitting comparison of conventional treatment costs to non-conventional treatments as they diverge from well-known diagnostic codes, i.e. International Classification of Diseases, 9th Revision, Clinical Modification (ICD-9-CM).

The American Medical Association currently controls the ICD-9-CM and current procedural terminology (CPT) codes used to diagnose and to bill for conventional medicine. These codes are an insurance industry standard by which to bill and process medical claims by payers. Claims payment systems, relying on negotiations with providers for managed care solutions, depend on these coding systems to match charges with treatments, translate costs into statistics to identify costs, underwrite health insurance policies, and track patient outcomes and patient utilization.

As alternative medicine is brought into mainstream medicine, alternative providers have attempted to use these codes; but their claims are not understood by the payers because accurate descriptions of the services they perform do not exist therein.

Furthermore, ICD-9-CM and CPT codes do not identify the practitioner by profession. For these reasons, "dummy billing codes" or codes designed by individual payers to cope with payment for alternative treatments have been developed by a few carriers which offer payment benefits to alternative medicine. Likewise, state Medicaid and workers' compensation codes have been modified to cope with integration of acupuncture and naturopathy into each system.

In each of these instances, the source of the descriptions of alternative services or treatments originate not from schools or associations of alternative medicine which are able to properly identify and describe each treatment, but rather from the payers themselves. Therefore, unfortunately, these description codes are not comprehensive and fail to account for all services performed in the office of an alternative provider. Therefore, no independent system presently exists to cope with the need for the exchange of information in this field of health care, and none can be expected to evolve from CPT codes of the American Medical Association, whose mission is to promote treatments used by conventional medical doctors and which organization is not trained to understand alternative treatments. The present result is that alternative health care cannot be widely used by the existing payer systems, such as Medicare and Medicaid, until the descriptions of treatments by alternative practitioners is put into standardized terminology and given corresponding codes.

As an added complication, a working system must also incorporate the licensing and "scope of practice" regulations of each state in order to be useful to the payers.

Finally, alternative codes should be distinct from CPT. Cost outcome studies with conventional treatments depend on this distinction and are crucial to payers to underwrite the cost of adding alternative medicine and to meet consumer demand.

Thus, the present system and method takes advantage of the failures of the current coding system to provide accurate data and a universal terminology for alternative medicine in a state-specific format. By providing a system to which the alternative healthcare provider may attach a code to a valid description of services, the benefit of having alternative treatments added to insurance coverage can be attained.

No national system of encoding or processing alternative healthcare provider billing is known in the prior art. However, among traditional healthcare billing systems, several methods and systems are known. For example, U.S. Pat. No. 4,491,725, issued Jan. 1, 1985, to Pritchard, describes a medical claim verification and processing system in which a medicard is used to access a central brokerage computer for patient information for implementation of a method to rapidly determine an insurance claim payment for a specified patient service. The computer stores a code conversion table for each possible paying insurance carrier for converting patient treatment codes into service codes associated with a claim payment. The end result is an increase in the speed of processing of information, which enables the provider and patient to rapidly assess the current status of the payment of a claim by an insurance carrier. Such system fails to provide a method of encoding non-traditional types of healthcare treatments.

Moreover, such system and others like it apply only to preexisting systems of codes, such as CPT codes adopted by many insurance companies and the federal government for Medicare reimbursement. CPT codes are standard patient treatment codes, as set forth by the American Medical Association and adopted by the federal government for Medicare reimbursement claims. As part of a more comprehensive system, CPT codes set forth a five digit code to identify a particular type of procedure in each of five main procedure rubrics: Medicine; Anesthesia; Surgery; Radiology; and Pathology. Each code typically covers a category of specific medicinal procedures, as well as other ancillary information, such as the location of such procedure (e.g., emergency room, outpatient office visit, etc.) and the duration of such visit. Such information is requested by the payer to properly analyze whether reimbursement of payment claims for patient services by the provider is warranted. As noted, the CPT codes have become highly popular and are being adopted by insurance companies to analyze the appropriateness of a claim for payment.

However, CPTs are, at the least, cumbersome and expansive, and often confuse the practitioner which CPT code to use. For example, in cases where certain specialties perform procedures which cross many sub-specialties, the procedures fall into more than one of the numerated rubrics of CPT codes, and the burden on the practitioner to learn the proper classification becomes particularly undue.

Therefore, systems have been developed to try to automate the function of selecting the proper CPT code. For example, and as described in U.S. Pat. No. 5,325,293, issued Jun. 28, 1994, to Dorne, a system to correlate medical procedures and medical billing codes for interventional radiology procedures includes generating raw codes which correspond with selected medical procedures and then analyzes the raw codes to generate a set of intermediate codes, which account for the interrelation of the selected medical procedures, without altering the raw codes. The billing codes are then generated from the intermediate codes.

To determine appropriateness of a treatment for a procedure, even when the procedure has been properly classified under a CPT code, the procedure must be appropriate to the diagnosis before payment is made by a payer. Another system is discussed in U.S. Pat. No. 4,667,292, issued May 19, 1987, to Mohlenbrock, et al., wherein the use of a computer system is provided for identifying the most appropriate billing categories, namely Diagnosis Related Groups (DRGs), as also set forth by the federal government for Medicare reimbursement. The Medicare payment system requires first encoding diagnostic (ICD-9-CMs) and procedural (CPT) information, which steps are dependent upon several factors, including a principal diagnosis of the patient's problem, the procedures performed upon the patient, the age of the patient, and the presence or absence of any complications or co-morbidity, DRGs are determined in part by the ICD-9-CM coding system, which refers to a coding system based on a compatible with an accepted, original system of classification system provided by the World Health Organization. The ICD-9-CM codes are used in North America, being a classification of diseases, injuries, impairments, symptoms, medical procedures and causes of death. The ICD-9-CMs are initially divided into Disease and Procedure sections. These sections are further subdivided into subsections which encompass anywhere from 1–999 three digit disease or 1–99 two digit procedure code categories. Within the three digit code categories, there can be an additional 2 or digits to divide the codes into subcategories which further define either or both the disease manifestations and diagnostic procedures. There are approximately 15,000 ICD-9-CM codes, of which only a fraction are useful in the Medicare payment system, and even less are relevant to determining patient services of alternative healthcare providers.

The Mohlenbrock et al. System is clearly only directed at aiding in a determination which one of the large number of the predetermined list of payment categories is appropriate for reimbursement of a provider and providing a thorough and complete billing for maximum Medicare reimbursement under the Medicare system. Unlike the present system and method, the means are not directed at categorizing patient record and provider billing information by valid terminology and a corresponding code specific to alternative medicine and by state scope of practice for each provider type.

Other systems are also known for organizing medical information into useful codes. In U.S. Pat. No. 5,002,630, issued Mar. 19, 1991, to Wiltfong, a business system comprising means for coding client histories, listing plural procedures, terms or remarks used in a specific office or business with a distinct alphanumerical indicator. The coding of these factors is directed to sequencing veterinary procedures most frequently used in an office, and systemized into an index of broad categories called a procedural index in which each requires financial consideration to be entered when such procedure is provided. A chain of alphanumeric indicators can then be constructed to identify the procedure, terms or remarks. However, such system is directed not at systemizing the billing external to the office, but is primarily intended as an internal housekeeping measure.

None of the above inventions and patents, taken either singly or in combination, is seen to describe the instant invention as claimed.

SUMMARY OF THE INVENTION

The present invention relates to a method and system of encoding and processing healthcare provider billing, more particularly, a computer assisted network for encoding, documenting and processing claims for a payment of specific procedures by alternative therapy providers, grouped geographically and by specialty. The system employs a computer accessing three main databases for identifying, encoding and calculation of costs of provider services. A resulting Alternative Billing Code (ABC) is produced which can be compared and correlated with insurance industry standard codes. The ABC has the attribute of conveying multiple levels of information through alpha-numeric characters in a consistent manner which allows easy interpretation of the code. The ABC is an assembly of terms from three additional tables of terms stored in databases in the system, namely tables of Standard Alternative Procedure Descriptions (SAPDs), merged Provider Average Rates (PARs) and Relative Value Units (RVUs).

The SAPD is a database of terms of standard vocabulary and terminology used to describe alternative treatments for communication within the system. Expanded definitions for each SAPD will exist in a separate subdatabase within an ABC or SAPD field of each database for publication of the entire coding system.

The Provider Average Rate (PAR) is the average cost for a procedure performed by a hypothetical provider grouped by specialty and region. The PAR is calculated by taking a sampling of groups of at least 20 actual providers in a predetermined profession or specialty and geographical area and calculating an average rate for each procedure used. The highest and lowest 10% of provider charges are eliminated before the average rate is calculated.

RVU is a value unit given to a particular procedure, good or service which equates any one service relative to the value of all other services. A conversion factor is used to convert an RVU into a payment amount which is acceptable to all parties, the payer and the provider. When a provider becomes a member of a network using the ABC, the provider agrees to a set of conversion factors used by a payer, i.e. payment units, namely a fixed number of dollars. The relative cost of a procedure is derived by assigning a conversion factor for each branch of medicine, surgery, pathology, and radiology, coded M, S, P and R respectively. Data on existing conversion factors based on codes that crossover between conventional medicine and complementary medicine may be used to establish RVU conversion factors with a payer.

However, Relative Value Units (RVUs) may also be developed by surveying the prevalent provider service charges in an area where no data exists. The PAR is divided by the prevalent payer conversion factor as negotiated and according to the terms of a Provider Service Agreement under which a provider abides in order to use the RVU and associated conversion factor as offered by the payer. The conversion factor and RVU are each stored in an RVU database which contains every conversion factor rate for each payer as negotiated.

To make claim for payment under the system, a claim form from an alternative provider may be submitted by paper or by electronic transmission to a central database using the ABC or SAPD. The provider identifies the payer and the state wherein the claim for payment is filed. Such information is input into the computer assisted system and processed so as to retrieve from the RVU conversion factor database the conversion factor linked with the appropriate SAPD and policy plan, whereupon a price figure is calculated for the associated procedure (RVU×conversion factor).

The system then checks to see if the procedure is within the allowed scope of practice of the provider in the state where the claim was filed. Each provider using this system will have a list of allowed charges for the state in which the provider practices and a corresponding code to attach.

The system encourages alternative providers to join a managed care network using the ABC coding system to ascertain rates for services by 1) providing a provider's patient with the broadest possible coverage for alternative treatment claims and 2) assuring access by large populations subscribing to a particular payer to member alternative providers, thereby increasing the provider's patient base and in turn income. If the provider is not a member of such a network, any charges from the provider above the payer's usual and customary fee schedule, or all charges as in the case of an HMO, will become the liability of the patient.

Accordingly, it is a principal object of the invention to provide a comprehensive encoding system for handling payment claims made by alternative healthcare providers so that they have access to managed care contracts.

It is another object of the invention to provide a system in which provider price input conveys cost average information of a group of peer providers, particularly when no data otherwise exists for rates in a given geographic location or state.

Still another object of the invention is to provide a series of standardized terms corresponding to training standards to thereby create the SAPD and to organize this information so that alternative providers, as well as payers, can retrieve the information easily.

These and other objects of the invention will become readily apparent upon further review of the following specifications and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention relates to a method and system of encoding and processing healthcare provider billing, more particularly, a computer assisted network for encoding, documenting and processing fee charges for specific procedures of alternative healthcare providers, grouped geographically and by specialty, which fee charges are further verified as appearing within a predetermined scope of practice of a provider as geographically grouped.

Figure 1:
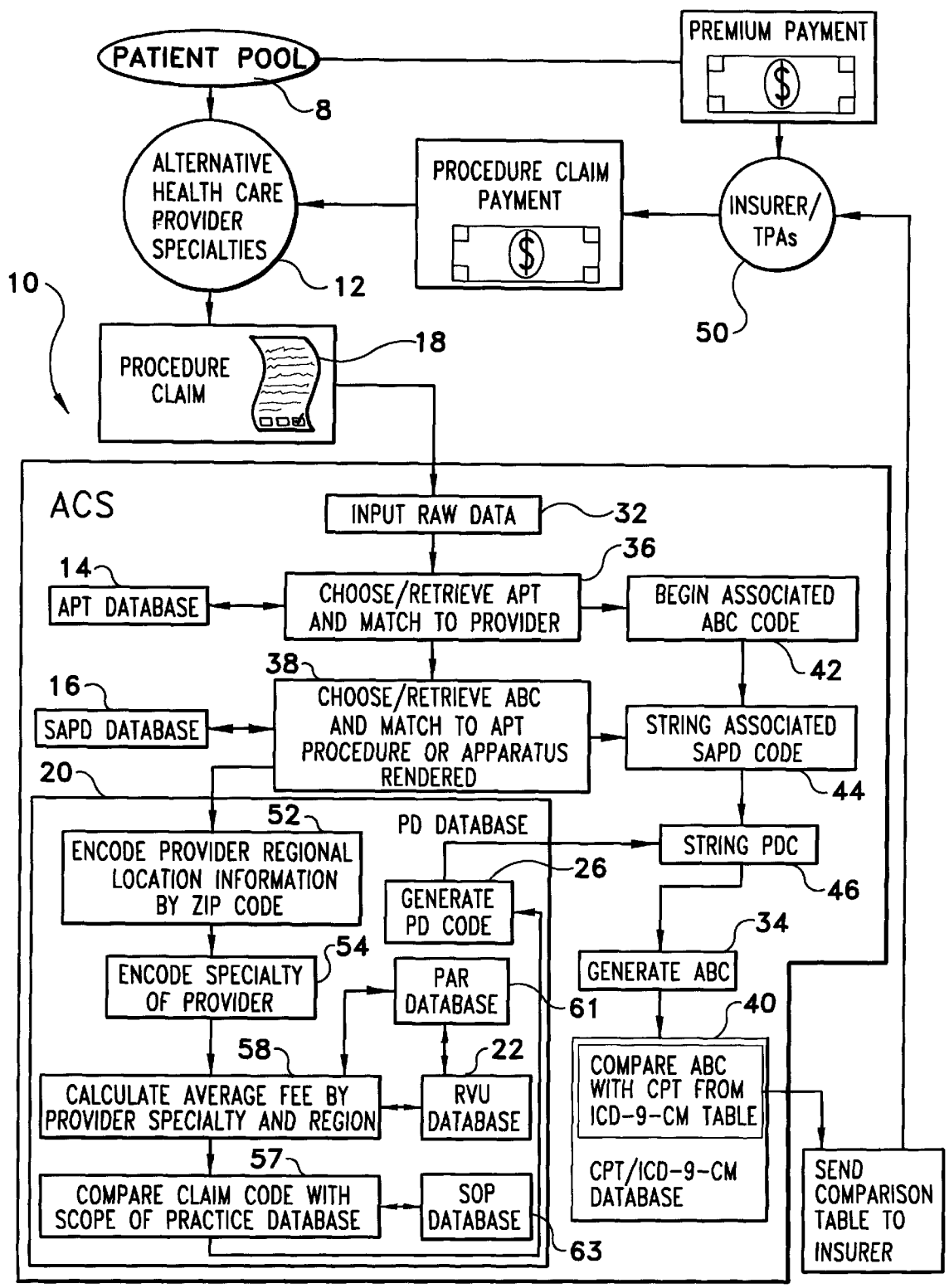
FIG. 1 is a block diagram in overview of the system and its method of use.

The system 10 is shown generally in overview in FIG. 1 and is named the Alternative Coding System (ACS). The system is provided to interact with alternative healthcare providers (herein "providers") 12, which comprise various specialties and sub-specialties. The table herein provides a suggested list of such provider specialties, which range from traditional medical arts, such as medicine by doctors and osteopaths, which require broad certification or licensing, and which arts are accepted by insurers as payable for treatment claims, to non-traditional arts, such as Homeopathy, which is currently not payable for treatment claims by most insurers. Other arts, such as Chiropractic, which has made a leap of acceptance into the insurance industry payment system, are included as well.

TABLE

| | |
|---|---|
| Accupressure | Pain Management |
| Acupuncture | Personal Fitness Training |
| Alexander Technique | Physical Therapy |
| Applied Kinesiology | Polarity |
| Aromatherapy | Psychiatry |
| Art Therapy | Psychology |
| Aston Patterning | Psychic Healing |
| Athletic Training | Psychoneuroimmunology |
| Ayurveda | Psychotherapy |
| Bioenergetics | Qi Gong |
| Breath Work | Reflexology |
| Chelation | Reichian Therapy |
| Chinese Massage | (Body & Mind) |
| Chiropracty | Rolfing |
| Crystal Healing | Rosen Method |
| Colonic Therapy | Sex Therapy |
| Communication Therapy | Shamanism |
| Craniosacral Therapy | Shiatsu |
| Curanderas/Sobendoras | Sleep Disorders |
| Dance Therapy | Social Work |
| Holistic Dentistry | Sound Therapy |
| Dream Therapy | Sports Therapy |
| Drama Therapy | Spiritual Healing |
| Faith Healing | Stress Management |
| Feldenkrais | Structural Integration |
| Functional Integration | Substance Abuse |
| Guided Imagery | Tai Chi |
| Hakomi Therapy | Touch for Health |
| Health Food Stores | Therapeutic Touch |
| Hellerwork | Trager Work |
| Herbal Medicine | Transition |
| Holistic Medicine | (Death Counseling) |
| Home Health Care | Tui Na |
| Homeopathy | Water (Pool) Therapy |
| Hospice | Holistic Wellness Medicine |
| Hypnotherapy | Yoga Therapy |

TABLE-continued

| | |
|---|---|
| Iridology | Massage Therapy |
| Midwifery | Music Therapy |
| Naturopathy | Neuromuscular Therapy |
| Nutrition Counseling | Native American Healing |
| Neurolinguistic Programming | Oriental/Chinese Medicine |
| Osteopathic Medicine | |

The list, although not comprehensive, is the basis for an encoding procedure yielding a multi-level and user-friendly code, called ABC (Alternative Billing Code) 34 generated by the system 10 through a series of encoding steps. The encoding process includes a series of steps 32,36,38,52,54, 57, each step encoding terms to represent cost input and code reports from any provider by state and zip code.

Unlike CPT codes, the ABC has the attribute of consistency in its assemblage whereby it can convey information through alphanumeric characters and hence multiple levels of information. Such code is generally described as an assembly of a series of terms and sub-terms chosen from four tables, namely tables of Alternative Practice Type (APT), Standardized Alternative Procedure Descriptions (SAPD), PD (Provider Data), and Relative Value Units (RVU), each stored in databases 14,16,20,22 of the system. The RVU database 22 is generated from calculations from the provider enrollment packet as grouped by specialty and region and is therefore included as a subdatabase within the PD database 20.

For example, each specialty listed on the Table defines a general provider category into which specific treatment or procedures may fall, each category having an alphabetic code term assigned to it, such as CH for Chiropractic. Thus, a rubric is created and designated by the code "CH" for all chiropractic procedure charges. This two-letter code allows the system to isolate all procedures within the scope of practice (SOP) of chiropractors. This provides the basis of the Alternative Practice Type (APT) table. Therefore each APT table would, for example, contain a listing for the rubric of Chiropractic, "CH," or Midwife "MW," thereby defining a category by which the system separates other information, such as cost averages and scope of practice, relevant to each profession or specialty.

Because present medical terminology is inadequate for the breadth of terminology needed to adequately define each of the procedures and the like of alternative healthcare, each of the specialties may form associations to help implement, evaluate, modify or otherwise present suggested code terms, abbreviations, lists of procedures, apparatus, health foods, and other details of treatment regarding their own specialty. As in traditional medicine having CPTs, the resulting table, the SAPD table, stored in the SAPD database 16 of the system, is a comprehensive listing of procedures, apparatus and professions and the like for each specialty and for each category of APT.

Referring again to FIG. 1, the Alternative Coding System (ACS) 10 includes an operable computer system having components of any platform type having programmable memory and a central processing unit (cpu). In the computer system, the APT tables are stored in and retrievable from the APT database 14 and the SAPD tables are stored in and retrievable from SAPD database 16. Thus, when a patient from the patient pool 8 is seen by a provider 12, a claim form 18 for payment of services and treatment as provided by a participating specialist is submitted to ACS 10 for encoding. At later stages of development of ACS use, it is foreseen that each provider 12 is provided with electronic means to communicate with ACS, either by computer terminal with remote communications means such as modem, or Internet e-mail. Such connections would provide interactive means for communicating appropriate code term information such that the encoding process may begin in the provider's office. Thus, such claim form 18 may be submitted either in the traditional hard copy from sent by mail or the like, or by remote electronic communications means such as by the internet.

To become a participating specialist, a provider may apply to ACS and be provided with a membership code (or the PD code as shown in block 26) for storage in the Provider Data (PD) database 20. The membership code contains various information based upon a minimum disclosure by the provider of name, specialty and regional location information, preferably by zip code of the principal office address. For example, a representative code would appear MT88046, in which the term "MT" represents the specialty, massage therapy, as chosen from the APT database 14 and resulting from the input raw data step 32. The term 88046 is the zip code attached to the APT code, thus forming a link in the chain of terms forming the provider membership code.

The zip code portion of the membership code stored in the PD database 20 is the basis for subsequent comparison of scope of practice codes defining the limits of allowable fees and regulated procedures as legislated from state to state. The state scope of practice is identified by any suitable codes defining such scope, and includes a zip code identifying portion and is stored in the SOP database 63. The zip code portion of the membership codes subsequently encoded onto the incoming claims entered at the input step 32 are then correlated with the zip code portions of the scope of practice database 63 in order to establish proper claims payment. This step of the encoding process may occur at any point in the processing of a claim after the membership code has been established and correlated with the service or procedure claimed, such as suggested by block 57.

When a participating provider accesses ACS 10, the claim form 18 having raw information including both the patient information and the minimum provider information or data (including provider fee, or in the alternative, an RVU adjusted amount claimed for each service rendered) is input for translation (at 32) into an encoded form. Means for inputting the raw information is provided, which may include a keyboard or scanning means. The cpu is programmed to store such information in an appropriate memory file and access the databases 14,16. The APT database 14 is accessed and provider specialty is matched to the appropriate APT code and retrieved 38. Likewise, the patient treatment by procedure or prescribed apparatus is matched to the appropriate SAPD code which is retrieved 38 and encoded to the claim. Having retrieved the appropriate code terms, the code terms are sequentially linked by the central processing unit to form an intermediate code term comprising the portion of the ABC 34 including the SAPD and APT. In the previously noted example and referring momentarily to FIG. 2, the intermediate code term portion may be "CH" 24 for the SAPD code 29 for a chiropractic spinal manipulation. A stringed code portion of the final PD code, including category and sub-category, is thus generated.

The stringed code terms are input into the PD database 20 and a PD file is created for each combination of diagnosis and procedure for use with the following steps. The PD database 20 contains all PD files for retrieval and calculation of a cost average of the total claims presented for a specific SAPD and APT combination grouped by provider specialty and location. The cpu is programmed to group each provider by the regional location of the provider 52, preferably by using zip code or state and its associated code, and by specialty 54, according to the APT code.

Thus, for example, a claim submitted for payment may be the chiropractic spinal manipulation, which is stored in a PD file.

The claim associated with it for payment may be, for example, $24. As calculated in the system (step 58) according to the appropriate formula, RVU×conversion factor= payment amount, or 4×$6=$24, the twenty-four dollar charge for payment of the claim is then compared with the remaining PD files for providers as encoded for a predetermined region matching the claim code. The predetermined region may be identified by zip code or by a broader region including numerous zip codes, or alternatively, in a subregion by RVU conversion factor for the carrier. Thus, if the conversion factor is $6 as negotiated for the New Mexico region, the system is programmed to multiply $6×RVU. The claimed payment of $24 matches the formula calculation and is therefore payable, which information is stored in the PD file generated at block 26. Using this system, claims payment determinations by third-party payers may also be made based upon this information.

The system at step 58 also calculates a Provider Average Rate (PAR), which is the average cost for a procedure performed by a hypothetical provider grouped by specialty and region. The PAR is calculated by taking a sampling of groups of at least 20 actual providers in a predetermined profession or specialty and geographical area and calculating an average rate for each procedure used, as based on inputted claims information. The highest and lowest 10% of provider charges are eliminated before the average rate is calculated. This information is stored in the PAR database 61.

Upon calculation of the cost, the PD file of step 26 is now processed to combine the SAPD, and APT (from blocks 42, 44, 46) to yield the ABC 34, a single code that represents all the necessary elements incident to treatment. Clearly, each portion of the alphanumeric codes, as discussed above, may be associated into a string having a consistently organized and standard format, which is repeated for each SAPD and APT to provide an intuitive and user-friendly code.

Such ABC is used to provide insurance carriers and other third-party payers (at 50) with the PD code portion and other encoded cost data for payment of the provider's claim 18. However, as such insurance carriers are generally not familiar internally with a method of processing alternative healthcare provider claims, a conversion table is necessary to convert the ABC 34 to the traditionally accepted forms of coding, such as CPTs. The relative cost of a procedure is typically derived by assigning a conversion factor for each branch of medicine, surgery, pathology, and radiology, coded M, S, P and R respectively. Therefore, a conversion database 40 is provided containing a table of corresponding CPT and ICD-9-CM codes to help the payer translate the information from the ABC, shown by the "AM" designation representing an "alternative medicine" code in FIG. 3.

Figure 2:
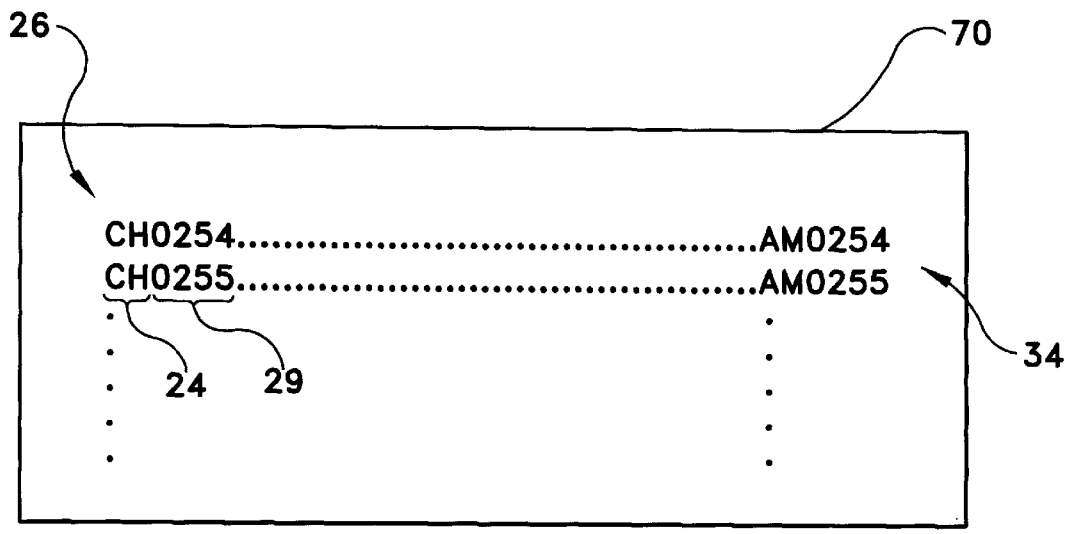
FIG. 2 is a diagrammatic representation of an exemplary conversion table for tracking PD codes as converted to the ABC code.

The present ACS encoding system 10 is compatible with such typical format. FIG. 2 is the code conversion table 70 used in tracking individual procedure costs used in building the ABC, shown at 34. In the left column, each of the PD codes 26 are listed as the standard patient treatment codes for each provider type. Entire ABC codes 34 may be listed in which the PD code is included, shown in the right column.

Figure 3:
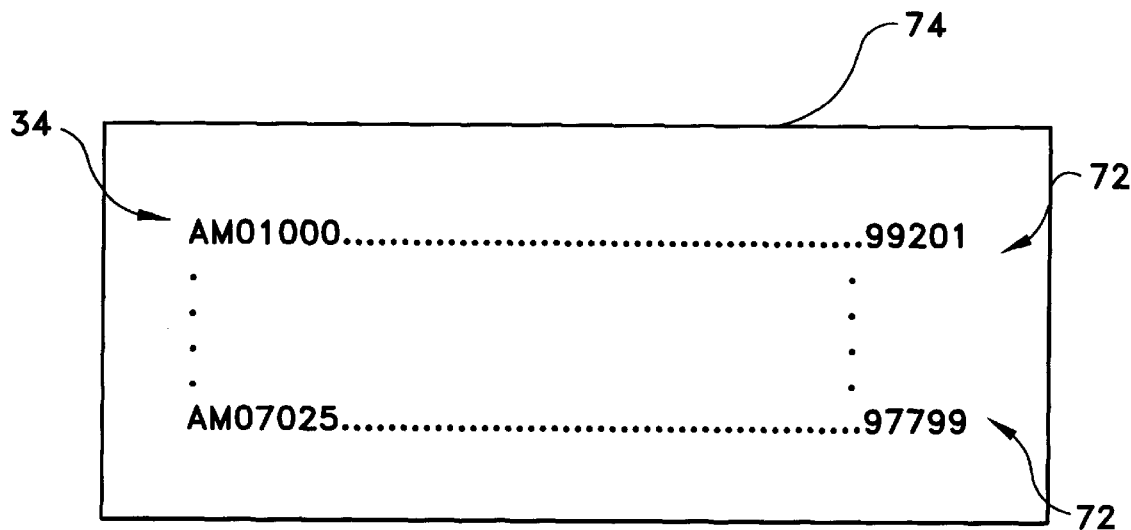
FIG. 3 is a diagrammatic representation of an exemplary code conversion table from ABC codes of the present invention to CPT or similar codes.

To convert this information to a useful format familiar to an insurance carrier, FIG. 3 illustrates a code conversion table 74 for a particular insurance carrier. The ABC codes 34 can be converted by means of such conversion table 74 into a specific RVU and conversion factor codes of a given insurance carrier. Upon review of each table, the insurance carrier can thus correlate the right column of the conversion table 70 (exclusively for use with alternative medicine) with the appropriate service code numbers (CPT codes) 72 of the left column of the conversion table 74 as used by the insurance industry.

Ultimately, claims processing fees may pass along a cost operating the ACS system plus reasonable profits. A set user fee may be charged to the provider to process claims.

It is understood that the present invention is not limited to the sole embodiment described above, but encompasses any and all embodiments within the scope of the following claims.

I claim:

1. A method of encoding, documenting and processing the procedures and billing of alternative healthcare provider treatment, using a computer system having a programmable memory and central processing unit, comprising the steps of:

inputting and encoding a database of a plurality of alternative healthcare providers each categorized with an alphanumeric indicia to yield an alternative practice type (APT) code;

inputting and encoding a database of alternative procedures for each of the plurality of alternative healthcare provider categories by an alphanumeric indicia to yield a standard alternative procedure descriptions SAPD code;

stringing the SAPD and alternative practice type APT codes together to yield a string;

inputting and encoding a relative value units RVU database including a conversion factor and RVU for each string;

inputting and encoding claims information from alternative healthcare providers and patients including specialty, regional location, each procedure and prescription item prescribed and grouping each provider by region and by specialty;

calculating a provider charge for each procedure and prescription item prescribed by multiplying the RVU by the conversion factor;

encoding the provider charge in an RVU code and stringing it to the string to yield a PD code; and stringing the PD code and a RVU code to yield an alternative billing code.

2. The method according to claim 1, further including the step of providing insurance carriers and third-party payers with a standardized alternative procedure description.

3. The method according to claim 1, further including the step of equating the SAPD with CPT used in the insurance industry and preparing a conversion table.

4. The method according to claim 1, wherein the step of inputting the regional location of a specialty and provider includes determining the zip code and state.

5. The method according to claim 1, wherein the step of grouping includes grouping by zip code and state.

6. The method according to claim 1, further comprising the step of obtaining patient records and translating raw patient information into input data.

7. The method according to claim 1, further comprising the step of supplementing the alternative billing codes and alternative procedural terminology with additional codes and terminology.

8. A programmed computer assembly for encoding, documenting and processing the procedures and billing of alternative healthcare provider treatment, comprising a computer having programmable memory and central processing unit, a program installed on the computer having means for inputting and encoding a database of a plurality of alternative healthcare providers each categorized by an alphanumeric indicia to yield an alternative practice type (APT) code;

means for inputting and encoding a database of alternative procedures for each of the plurality of alternative healthcare provider categories with an alphanumeric indicia to yield an SAPD code;

means for stringing the standard alternative procedure descriptions SAPD and APT codes together to yield a string;

means for inputting and encoding a RVU database including a conversion factor and relative value units RVU for each string;

means for inputting and encoding claims information from alternative healthcare providers and patients including specialty, regional location, each procedure and prescription item prescribed and grouping each provider by region and by specialty;

means for calculating a provider charge for each procedure and prescription item prescribed by multiplying the RVU by the conversion factor;

means for encoding the provider charge in an RVU code and stringing it to the string to yield a PD code; and means for stringing the PD code and a RVU code to yield an alternative billing code.

9. The programmed computer assembly according to claim 8, wherein the program further has a means of comparing the alternative terminology code with accepted CPT codes used in the insurance industry and preparing a conversion table.

10. The programmed computer assembly according to claim 8, wherein the program further has means for determining a state code from input information and grouping associated information by state to identify licensing and scope of practice of providers.

* * * * *